(12) United States Patent
Lindenbaum et al.

(10) Patent No.: US 8,372,072 B2
(45) Date of Patent: ***Feb. 12, 2013

(54) METHODS AND APPARATUS FOR HEMOSTASIS FOLLOWING ARTERIAL CATHETERIZATION

(75) Inventors: Hayim Lindenbaum, Haifa (IL); Shimon Eckhouse, Haifa (IL)

(73) Assignee: Cardiodex Ltd., Cesarea Business Park (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/302,662

(22) Filed: Nov. 22, 2011

(65) Prior Publication Data

US 2012/0065637 A1 Mar. 15, 2012

Related U.S. Application Data (63) Continuation of application No. 11/797,294, filed on May 2, 2007, now abandoned, which is a continuation of application No. 10/616,887, filed on Jul. 10, 2003, now Pat. No. 7,223,266, which is a continuation-in-part of application No. 10/358,130, filed on Feb. 4, 2003, now Pat. No. 7,115,127.

(51) Int. Cl.
*A61B 18/14* (2006.01)

(52) U.S. Cl. .......................... 606/49; 606/213

(58) Field of Classification Search ............ 606/27, 606/40–41, 49–50, 192, 194, 213; 604/96.01–104
See application file for complete search history.

(56) References Cited

U.S. PATENT DOCUMENTS

| | | |
|---|---|---|
| 524,417 A | 8/1894 | Fahey |
| 1,596,004 A | 8/1926 | De Bengoa |
| 1,731,069 A | 10/1929 | Herman |
| 1,881,250 A | 10/1932 | Tomlinson |
| 1,983,669 A | 12/1934 | Kimble |
| 2,144,090 A | 1/1939 | Spencer |
| 2,790,442 A | 4/1957 | Donaldson |
| 2,808,833 A | 10/1957 | August |
| 3,100,489 A | 8/1963 | Bagley |
| 3,176,114 A | 3/1965 | Kneisley |
| 3,301,258 A | 1/1967 | Werner et al. |
| 3,302,635 A | 2/1967 | Pittman |
| 3,494,364 A | 2/1970 | Peters |
| 3,500,828 A | 3/1970 | Podhora |
| 3,532,095 A | 10/1970 | Miller |
| 3,595,238 A | 7/1971 | Gavrilov et al. |
| 3,613,682 A | 10/1971 | Naylor |
| 3,636,943 A | 1/1972 | Balamuth |
| 3,699,967 A | 10/1972 | Anderson |
| 3,794,040 A | 2/1974 | Balamuth |

(Continued)

FOREIGN PATENT DOCUMENTS

| | | |
|---|---|---|
| CA | 2514865 A1 | 8/2004 |
| CA | 2587228 A1 | 5/2006 |

(Continued)

OTHER PUBLICATIONS

U.S. Appl. No. 60/630,245, filed Nov. 22, 2004, Mizrahi et al.

(Continued)

*Primary Examiner* — Michael Peffley
*Assistant Examiner* — Samantha Good
(74) *Attorney, Agent, or Firm* — Venable LLP (57) ABSTRACT

A method for producing hemostasis of an artery of a patient having a puncture following arterial catheterization including introducing a hemostasis device including at least one electrode into the vicinity of the puncture, supplying an electric current to the at least one electrode, thereby heating blood in the vicinity of the puncture and causing coagulation of the blood and subsequently removing the hemostasis device from the patient.

16 Claims, 11 Drawing Sheets

U.S. PATENT DOCUMENTS

| | | |
|---|---|---|
| 3,801,766 A | 4/1974 | Morrison, Jr. |
| 3,801,800 A | 4/1974 | Newton |
| 3,825,004 A | 7/1974 | Durden, III |
| 3,858,586 A | 1/1975 | Lessen |
| 3,874,388 A | 4/1975 | King et al. |
| 3,886,944 A | 6/1975 | Jamshidi |
| 3,920,021 A | 11/1975 | Hiltebrandt |
| 3,929,137 A | 12/1975 | Gonser |
| 3,938,527 A | 2/1976 | Rioux et al. |
| 3,963,030 A | 6/1976 | Newton |
| 3,978,863 A | 9/1976 | Fettel et al. |
| 3,980,085 A | 9/1976 | Ikuno |
| 4,003,380 A | 1/1977 | Wien |
| 4,007,743 A | 2/1977 | Blake |
| 4,011,872 A | 3/1977 | Komiya |
| 4,014,343 A | 3/1977 | Esty |
| 4,016,881 A | 4/1977 | Rioux et al. |
| 4,043,342 A | 8/1977 | Morrison, Jr. |
| 4,051,855 A | 10/1977 | Schneiderman |
| 4,054,143 A | 10/1977 | Bauer |
| 4,074,718 A | 2/1978 | Morrison, Jr. |
| 4,112,950 A | 9/1978 | Pike |
| 4,122,853 A | 10/1978 | Smith |
| 4,162,673 A | 7/1979 | Patel |
| 4,168,708 A | 9/1979 | Lepley, Jr. et al. |
| 4,198,957 A | 4/1980 | Cage et al. |
| 4,202,337 A | 5/1980 | Hren et al. |
| 4,211,230 A | 7/1980 | Woltosz |
| 4,215,699 A | 8/1980 | Patel |
| 4,228,800 A | 10/1980 | Degler, Jr. et al. |
| 4,230,119 A | 10/1980 | Blum |
| 4,269,174 A | 5/1981 | Adair |
| 4,271,839 A | 6/1981 | Fogarty et al. |
| 4,271,847 A | 6/1981 | Stokes |
| 4,273,127 A | 6/1981 | Auth et al. |
| 4,303,073 A | 12/1981 | Archibald |
| 4,314,555 A | 2/1982 | Sagae |
| 4,314,559 A | 2/1982 | Allen |
| 4,317,445 A | 3/1982 | Robinson |
| 4,327,709 A | 5/1982 | Hanson et al. |
| 4,352,924 A | 10/1982 | Wooten et al. |
| 4,353,371 A | 10/1982 | Cosman |
| 4,359,052 A | 11/1982 | Staub |
| 4,364,392 A | 12/1982 | Strother et al. |
| 4,370,980 A | 2/1983 | Lottick |
| 4,390,018 A | 6/1983 | Zukowski |
| 4,404,971 A | 9/1983 | LeVeen et al. |
| 4,411,266 A | 10/1983 | Cosman |
| 4,418,692 A | 12/1983 | Guay |
| 4,424,833 A | 1/1984 | Spector et al. |
| 4,470,415 A | 9/1984 | Wozniak |
| 4,476,862 A | 10/1984 | Pao |
| 4,481,057 A | 11/1984 | Beard |
| 4,483,338 A | 11/1984 | Bloom et al. |
| 4,492,231 A | 1/1985 | Auth |
| 4,498,475 A | 2/1985 | Schneiderman |
| 4,520,823 A | 6/1985 | LeVeen et al. |
| 4,522,205 A | 6/1985 | Taylor et al. |
| 4,532,924 A | 8/1985 | Auth et al. |
| 4,539,987 A | 9/1985 | Nath et al. |
| 4,548,207 A | 10/1985 | Reimels |
| 4,625,724 A | 12/1986 | Suzuki et al. |
| 4,637,392 A | 1/1987 | Sorochenko |
| 4,645,491 A | 2/1987 | Evans |
| 4,654,024 A | 3/1987 | Crittenden et al. |
| 4,671,274 A | 6/1987 | Sorochenko |
| 4,672,969 A | 6/1987 | Dew |
| 4,682,596 A | 7/1987 | Bales et al. |
| 4,708,136 A | 11/1987 | Saito |
| 4,709,698 A | 12/1987 | Johnston et al. |
| 4,716,897 A | 1/1988 | Noguchi et al. |
| 4,717,381 A | 1/1988 | Papantonakos |
| 4,735,201 A | 4/1988 | O'Reilly |
| 4,744,359 A | 5/1988 | Hatta et al. |
| 4,744,364 A | 5/1988 | Kensey |
| 4,760,847 A | 8/1988 | Vaillancourt |
| 4,765,331 A | 8/1988 | Petruzzi et al. |
| 4,776,349 A | 10/1988 | Nashef et al. |
| 4,790,819 A | 12/1988 | Li et al. |
| 4,801,293 A | 1/1989 | Jackson |
| 4,832,688 A | 5/1989 | Sagae et al. |
| 4,834,725 A | 5/1989 | Iwatschenko |
| 4,836,204 A | 6/1989 | Landymore et al. |
| 4,848,337 A | 7/1989 | Shaw et al. |
| 4,848,339 A | 7/1989 | Rink et al. |
| 4,848,352 A | 7/1989 | Pohndorf et al. |
| 4,850,960 A | 7/1989 | Grayzel |
| 4,852,568 A | 8/1989 | Kensey |
| 4,854,320 A | 8/1989 | Dew et al. |
| 4,860,745 A | 8/1989 | Farin et al. |
| 4,869,248 A | 9/1989 | Narula |
| 4,890,612 A | 1/1990 | Kensey |
| 4,900,303 A | 2/1990 | Lemelson |
| 4,917,089 A | 4/1990 | Sideris |
| 4,920,980 A | 5/1990 | Jackowski |
| 4,921,478 A | 5/1990 | Solano et al. |
| 4,929,246 A * | 5/1990 | Sinofsky ........................ 606/8 |
| 4,938,761 A | 7/1990 | Ensslin |
| 4,943,290 A | 7/1990 | Rexroth et al. |
| 4,946,463 A | 8/1990 | Wright |
| 4,953,559 A | 9/1990 | Salerno |
| 4,960,133 A | 10/1990 | Hewson |
| 4,961,729 A | 10/1990 | Vaillancourt |
| 4,979,948 A | 12/1990 | Geddes et al. |
| 4,994,060 A | 2/1991 | Rink et al. |
| 5,002,051 A | 3/1991 | Dew et al. |
| 5,006,119 A | 4/1991 | Acker et al. |
| 5,009,656 A | 4/1991 | Reimels |
| 5,013,312 A | 5/1991 | Parins et al. |
| 5,021,059 A | 6/1991 | Kensey et al. |
| 5,035,695 A | 7/1991 | Weber, Jr. et al. |
| 5,038,789 A | 8/1991 | Frazin |
| 5,047,025 A | 9/1991 | Taylor et al. |
| 5,047,028 A | 9/1991 | Qian |
| 5,049,148 A | 9/1991 | Mehl |
| 5,053,046 A | 10/1991 | Janese |
| 5,057,105 A | 10/1991 | Malone et al. |
| 5,061,267 A | 10/1991 | Zeiher |
| 5,061,274 A | 10/1991 | Kensey |
| 5,073,166 A | 12/1991 | Parks et al. |
| 5,078,743 A | 1/1992 | Mikalov et al. |
| 5,080,660 A | 1/1992 | Buelna |
| 5,085,659 A | 2/1992 | Rydell |
| 5,087,256 A | 2/1992 | Taylor et al. |
| 5,088,997 A | 2/1992 | Delahuerga et al. |
| 5,103,804 A | 4/1992 | Abele et al. |
| 5,108,392 A | 4/1992 | Spingler |
| 5,108,420 A | 4/1992 | Marks |
| 5,108,421 A | 4/1992 | Fowler |
| RE33,925 E | 5/1992 | Bales et al. |
| 5,116,332 A | 5/1992 | Lottick |
| 5,122,137 A | 6/1992 | Lennox |
| 5,122,139 A | 6/1992 | Sutter |
| 5,129,882 A | 7/1992 | Weldon et al. |
| 5,131,394 A | 7/1992 | Gehlbach |
| 5,133,714 A | 7/1992 | Beane |
| 5,141,515 A | 8/1992 | Eberbach |
| 5,147,316 A | 9/1992 | Castillenti |
| 5,147,357 A | 9/1992 | Rose et al. |
| 5,151,098 A | 9/1992 | Loertscher |
| 5,151,102 A | 9/1992 | Kamiyama et al. |
| 5,156,613 A | 10/1992 | Sawyer |
| 5,158,561 A | 10/1992 | Rydell et al. |
| 5,159,925 A | 11/1992 | Neuwirth et al. |
| 5,178,620 A | 1/1993 | Eggers et al. |
| 5,183,464 A | 2/1993 | Dubrul et al. |
| 5,188,602 A | 2/1993 | Nichols |
| 5,188,634 A | 2/1993 | Hussein et al. |
| 5,190,541 A | 3/1993 | Abele et al. |
| 5,192,300 A | 3/1993 | Fowler |
| 5,192,302 A | 3/1993 | Kensey et al. |
| 5,207,675 A | 5/1993 | Canady |
| 5,211,624 A | 5/1993 | Cinberg et al. |
| 5,215,103 A | 6/1993 | Desai |
| 5,217,024 A | 6/1993 | Dorsey et al. |
| 5,217,451 A | 6/1993 | Freitas |
| 5,217,458 A | 6/1993 | Parins |

| | | | | | | |
|---|---|---|---|---|---|---|
| 5,217,459 A | 6/1993 | Kamerling | 5,951,589 A | 9/1999 | Epstein et al. | |
| 5,217,460 A | 6/1993 | Knoepfler | 5,964,782 A | 10/1999 | Lafontaine et al. | |
| 5,220,924 A | 6/1993 | Frazin | 5,984,950 A | 11/1999 | Cragg et al. | |
| 5,221,259 A | 6/1993 | Weldon et al. | 6,002,361 A | 12/1999 | Schipper | |
| 5,221,281 A | 6/1993 | Klicek | 6,007,563 A | 12/1999 | Nash et al. | |
| 5,222,974 A | 6/1993 | Kensey et al. | 6,022,336 A | 2/2000 | Zadno-Azizi et al. | |
| 5,226,908 A | 7/1993 | Yoon | 6,022,361 A | 2/2000 | Epstein et al. | |
| 5,230,349 A | 7/1993 | Langberg | 6,033,398 A | 3/2000 | Farley et al. | |
| 5,257,635 A | 11/1993 | Langberg | 6,033,401 A | 3/2000 | Edwards et al. | |
| 5,258,000 A | 11/1993 | Gianturco | 6,045,569 A | 4/2000 | Kensey et al. | |
| 5,258,006 A | 11/1993 | Rydell et al. | 6,048,358 A | 4/2000 | Barak | |
| 5,269,780 A | 12/1993 | Roos | 6,056,768 A | 5/2000 | Cates et al. | |
| 5,275,616 A | 1/1994 | Fowler | 6,056,769 A | 5/2000 | Epstein et al. | |
| 5,277,696 A | 1/1994 | Hagen | 6,063,085 A * | 5/2000 | Tay et al. | 606/50 |
| 5,281,216 A | 1/1994 | Klicek | 6,071,277 A | 6/2000 | Farley et al. | |
| 5,282,799 A | 2/1994 | Rydell | 6,071,300 A | 6/2000 | Brenneman et al. | |
| 5,282,827 A | 2/1994 | Kensey et al. | 6,080,183 A | 6/2000 | Tsugita et al. | |
| 5,290,310 A | 3/1994 | Makower et al. | 6,090,130 A | 7/2000 | Nash et al. | |
| 5,292,332 A | 3/1994 | Lee | 6,104,291 A | 8/2000 | Beauvillier et al. | |
| 5,304,117 A | 4/1994 | Wilk | 6,111,424 A | 8/2000 | Bosacchi | |
| 5,304,214 A | 4/1994 | DeFord et al. | 6,113,598 A | 9/2000 | Baker | |
| 5,306,254 A | 4/1994 | Nash et al. | 6,120,524 A | 9/2000 | Taheri | |
| 5,320,639 A | 6/1994 | Rudnick | 6,126,635 A | 10/2000 | Simpson et al. | |
| 5,324,306 A | 6/1994 | Makower et al. | 6,142,994 A | 11/2000 | Swanson et al. | |
| 5,342,359 A | 8/1994 | Rydell | 6,152,920 A | 11/2000 | Thompson et al. | |
| 5,342,393 A | 8/1994 | Stack | 6,179,832 B1 | 1/2001 | Jones et al. | |
| 5,349,166 A | 9/1994 | Taylor | 6,179,863 B1 | 1/2001 | Kensey et al. | |
| 5,364,389 A | 11/1994 | Anderson | 6,217,574 B1 | 4/2001 | Webster | |
| 5,370,660 A | 12/1994 | Weinstein et al. | 6,228,082 B1 | 5/2001 | Baker et al. | |
| 5,383,896 A | 1/1995 | Gershony et al. | 6,235,027 B1 | 5/2001 | Herzon | |
| 5,383,899 A | 1/1995 | Hammerslag | 6,267,758 B1 | 7/2001 | Daw et al. | |
| 5,411,520 A | 5/1995 | Nash et al. | 6,287,322 B1 | 9/2001 | Zhu et al. | |
| 5,413,571 A | 5/1995 | Katsaros et al. | 6,306,133 B1 | 10/2001 | Tu et al. | |
| 5,415,657 A | 5/1995 | Taymor-Luria | 6,315,787 B1 | 11/2001 | Tsugita et al. | |
| 5,417,689 A | 5/1995 | Fine | 6,322,559 B1 | 11/2001 | Daulton et al. | |
| 5,419,195 A | 5/1995 | Quinn | 6,350,274 B1 | 2/2002 | Li | |
| 5,419,765 A | 5/1995 | Weldon et al. | 6,352,533 B1 | 3/2002 | Ellman et al. | |
| 5,431,639 A | 7/1995 | Shaw | 6,368,341 B1 | 4/2002 | Abrahamson | |
| 5,437,631 A | 8/1995 | Janzen | 6,371,964 B1 | 4/2002 | Vargas et al. | |
| 5,441,517 A | 8/1995 | Kensey et al. | 6,371,974 B1 | 4/2002 | Brenneman et al. | |
| 5,454,833 A | 10/1995 | Boussignac et al. | 6,398,780 B1 | 6/2002 | Farley et al. | |
| 5,458,573 A | 10/1995 | Summers | 6,398,782 B1 | 6/2002 | Pecor et al. | |
| 5,486,195 A | 1/1996 | Myers et al. | 6,402,745 B1 | 6/2002 | Wilk | |
| 5,507,744 A | 4/1996 | Tay et al. | 6,409,739 B1 | 6/2002 | Nobles et al. | |
| 5,540,715 A | 7/1996 | Katsaros et al. | 6,443,947 B1 | 9/2002 | Marko et al. | |
| RE35,330 E | 9/1996 | Malone et al. | 6,450,989 B2 | 9/2002 | Dubrul et al. | |
| 5,593,406 A | 1/1997 | Eggers et al. | 6,451,007 B1 | 9/2002 | Koop et al. | |
| 5,611,798 A | 3/1997 | Eggers | 6,468,272 B1 | 10/2002 | Koblish et al. | |
| 5,624,452 A | 4/1997 | Yates | 6,482,179 B1 | 11/2002 | Chu et al. | |
| 5,626,601 A | 5/1997 | Gershony et al. | 6,503,247 B2 | 1/2003 | Swartz et al. | |
| 5,630,833 A | 5/1997 | Katsaros et al. | 6,508,828 B1 | 1/2003 | Akerfeldt et al. | |
| 5,645,566 A | 7/1997 | Brenneman et al. | 6,511,479 B2 | 1/2003 | Gentelia et al. | |
| 5,654,566 A | 8/1997 | Johnson | 6,512,458 B1 | 1/2003 | Kobayashi et al. | |
| 5,676,689 A | 10/1997 | Kensey et al. | 6,529,756 B1 | 3/2003 | Phan et al. | |
| 5,700,277 A | 12/1997 | Nash et al. | 6,533,778 B2 | 3/2003 | Herzon | |
| 5,702,387 A | 12/1997 | Arts et al. | 6,537,299 B1 | 3/2003 | Hogendijk et al. | |
| 5,716,325 A | 2/1998 | Bonutti | 6,551,313 B1 | 4/2003 | Levin | |
| 5,716,375 A | 2/1998 | Fowler | 6,569,161 B2 | 5/2003 | Zappala | |
| RE35,755 E | 3/1998 | Qian | 6,569,182 B1 * | 5/2003 | Balceta et al. | 606/200 |
| 5,725,551 A | 3/1998 | Myers et al. | 6,589,237 B2 | 7/2003 | Woloszko et al. | |
| 5,728,122 A | 3/1998 | Leschinsky et al. | 6,593,853 B1 | 7/2003 | Barrett et al. | |
| 5,728,133 A | 3/1998 | Kontos | 6,626,899 B2 | 9/2003 | Houser et al. | |
| 5,728,134 A * | 3/1998 | Barak | 606/214 | 6,626,901 B1 | 9/2003 | Treat et al. | |
| 5,746,755 A | 5/1998 | Wood et al. | 6,656,136 B1 | 12/2003 | Weng et al. | |
| 5,782,860 A | 7/1998 | Epstein et al. | 6,656,207 B2 | 12/2003 | Epstein et al. | |
| 5,782,861 A | 7/1998 | Cragg et al. | 6,657,447 B1 | 12/2003 | Parandoosh | |
| 5,810,810 A | 9/1998 | Tay et al. | 6,669,262 B1 | 12/2003 | Crotty, III et al. | |
| 5,836,945 A | 11/1998 | Perkins | 6,676,657 B2 | 1/2004 | Wood | |
| 5,853,421 A | 12/1998 | Leschinsky et al. | 6,676,685 B2 | 1/2004 | Pedros et al. | |
| 5,868,778 A | 2/1999 | Gershony et al. | 6,679,904 B2 | 1/2004 | Gleeson et al. | |
| 5,879,499 A | 3/1999 | Corvi | 6,682,526 B1 | 1/2004 | Jones et al. | |
| 5,891,138 A | 4/1999 | Tu et al. | 6,689,126 B1 | 2/2004 | Farley et al. | |
| 5,895,386 A | 4/1999 | Odell et al. | 6,712,804 B2 | 3/2004 | Roue et al. | |
| 5,906,636 A | 5/1999 | Casscells, III et al. | 6,712,806 B2 | 3/2004 | St. Germain et al. | |
| 5,911,719 A | 6/1999 | Eggers | 6,712,815 B2 | 3/2004 | Sampson et al. | |
| 5,922,009 A | 7/1999 | Epstein et al. | 6,719,257 B1 | 4/2004 | Greene et al. | |
| 5,928,266 A | 7/1999 | Kontos | 6,743,195 B2 | 6/2004 | Zucker | |
| 5,941,897 A | 8/1999 | Myers | 6,768,086 B2 | 7/2004 | Sullivan et al. | |
| 5,944,730 A | 8/1999 | Nobles et al. | 6,772,013 B1 | 8/2004 | Ingle et al. | |

| Patent Number | Date | Name |
|---|---|---|
| 6,780,177 B2 | 8/2004 | Shafirstein et al. |
| 6,814,743 B2 | 11/2004 | Chin et al. |
| 6,817,743 B2 | 11/2004 | Sharper |
| 6,840,666 B2 | 1/2005 | Enachescu et al. |
| 6,846,321 B2 | 1/2005 | Zucker |
| 6,860,880 B2 | 3/2005 | Treat et al. |
| 6,904,303 B2 | 6/2005 | Phan et al. |
| 6,908,463 B2 | 6/2005 | Treat et al. |
| 6,932,810 B2 | 8/2005 | Ryan |
| 6,939,363 B2 | 9/2005 | Åkerfeldt |
| 6,942,674 B2 | 9/2005 | Belef et al. |
| 6,960,206 B2 | 11/2005 | Keane |
| 6,969,397 B2 | 11/2005 | Ginn |
| 6,984,219 B2 | 1/2006 | Ashby et al. |
| 6,997,926 B2 | 2/2006 | Gellman et al. |
| 7,001,398 B2 | 2/2006 | Carley et al. |
| 7,008,441 B2 | 3/2006 | Zucker |
| 7,025,748 B2 | 4/2006 | Ashby |
| 7,029,489 B1 | 4/2006 | Ashby et al. |
| 7,033,352 B1 | 4/2006 | Gauthier et al. |
| 7,037,322 B1 | 5/2006 | Sing et al. |
| 7,070,597 B2 | 7/2006 | Truckai et al. |
| 7,073,509 B2 | 7/2006 | Tenerz et al. |
| 7,099,717 B2 | 8/2006 | Woodard et al. |
| 7,115,127 B2 * | 10/2006 | Lindenbaum et al. ......... 606/49 |
| 7,144,411 B2 | 12/2006 | Ginn et al. |
| 7,147,634 B2 | 12/2006 | Nesbitt |
| 7,151,442 B1 | 12/2006 | Nguyen |
| 7,153,301 B2 | 12/2006 | Swartz et al. |
| 7,154,283 B1 | 12/2006 | Weakley et al. |
| 7,160,297 B2 | 1/2007 | Nesbitt |
| 7,164,353 B2 | 1/2007 | Puleston et al. |
| 7,175,646 B2 | 2/2007 | Brenneman et al. |
| 7,184,811 B2 | 2/2007 | Phan et al. |
| 7,201,725 B1 | 4/2007 | Cragg et al. |
| 7,211,080 B2 | 5/2007 | Treat et al. |
| 7,223,266 B2 * | 5/2007 | Lindenbaum et al. ......... 606/49 |
| 7,225,992 B2 | 6/2007 | Forster |
| 7,257,450 B2 | 8/2007 | Auth et al. |
| 7,474,909 B2 | 1/2009 | Phan et al. |
| 7,850,685 B2 | 12/2010 | Kunis et al. |
| 2001/0003158 A1 | 6/2001 | Kensey et al. |
| 2001/0007070 A1 | 7/2001 | Stewart et al. |
| 2001/0029373 A1 | 10/2001 | Baker et al. |
| 2002/0002371 A1 | 1/2002 | Acker et al. |
| 2002/0022822 A1 | 2/2002 | Cragg et al. |
| 2002/0062130 A1 | 5/2002 | Jugenheimer et al. |
| 2002/0072761 A1 | 6/2002 | Abrams et al. |
| 2002/0133123 A1 | 9/2002 | Zucker |
| 2002/0156495 A1 | 10/2002 | Brenneman et al. |
| 2002/0193808 A1 | 12/2002 | Belef et al. |
| 2003/0005397 A1 | 1/2003 | Larsen |
| 2003/0055397 A1 * | 3/2003 | Zucker ......... 604/509 |
| 2003/0055454 A1 * | 3/2003 | Zucker ......... 606/213 |
| 2003/0093116 A1 | 5/2003 | Nowakowski |
| 2003/0109869 A1 | 6/2003 | Shadduck |
| 2003/0120256 A1 | 6/2003 | Lary et al. |
| 2003/0125766 A1 | 7/2003 | Ding |
| 2003/0153060 A1 | 8/2003 | Wilson et al. |
| 2003/0191479 A1 | 10/2003 | Thornton |
| 2003/0195498 A1 | 10/2003 | Treat et al. |
| 2003/0199863 A1 | 10/2003 | Swanson et al. |
| 2003/0236518 A1 | 12/2003 | Marchitto et al. |
| 2004/0006333 A1 | 1/2004 | Arnold et al. |
| 2004/0010298 A1 | 1/2004 | Altshuler et al. |
| 2004/0030348 A1 | 2/2004 | Peterson et al. |
| 2004/0068306 A1 | 4/2004 | Shadduck |
| 2004/0092913 A1 | 5/2004 | Hennings et al. |
| 2004/0102797 A1 | 5/2004 | Golden et al. |
| 2004/0153054 A1 | 8/2004 | Lindenbaum et al. |
| 2004/0153060 A1 | 8/2004 | Lindenbaum et al. |
| 2004/0158287 A1 | 8/2004 | Cragg et al. |
| 2004/0199155 A1 | 10/2004 | Mollenauer |
| 2004/0199226 A1 | 10/2004 | Shadduck |
| 2004/0215232 A1 | 10/2004 | Belhe et al. |
| 2004/0220562 A1 | 11/2004 | Garabedian et al. |
| 2004/0249324 A1 | 12/2004 | Louis |
| 2004/0249342 A1 | 12/2004 | Khosravi et al. |
| 2004/0267307 A1 | 12/2004 | Bagaoisan et al. |
| 2005/0038419 A9 | 2/2005 | Arnold et al. |
| 2005/0085854 A1 | 4/2005 | Ginn |
| 2005/0192654 A1 | 9/2005 | Chanduszko et al. |
| 2005/0209637 A1 | 9/2005 | Zhu et al. |
| 2005/0228443 A1 | 10/2005 | Yassinzadeh |
| 2005/0267522 A1 | 12/2005 | Yassinzadeh et al. |
| 2005/0273095 A1 | 12/2005 | Taimisto et al. |
| 2005/0277980 A1 | 12/2005 | Yassinzadeh |
| 2006/0089637 A1 | 4/2006 | Werneth et al. |
| 2006/0190066 A1 | 8/2006 | Worthen |
| 2006/0206121 A1 | 9/2006 | Chin et al. |
| 2006/0235376 A1 | 10/2006 | Lindenbaum et al. |
| 2006/0253072 A1 | 11/2006 | Pai et al. |
| 2006/0271032 A1 | 11/2006 | Chin et al. |
| 2006/0276836 A1 | 12/2006 | Bergin et al. |
| 2007/0010391 A1 | 1/2007 | Mikijelj et al. |
| 2007/0021746 A1 | 1/2007 | Taimisto et al. |
| 2007/0021770 A1 | 1/2007 | Brenneman et al. |
| 2007/0049968 A1 | 3/2007 | Sibbitt et al. |
| 2007/0055223 A1 | 3/2007 | Eckhouse et al. |
| 2007/0100232 A1 | 5/2007 | Hiller et al. |
| 2007/0198057 A1 | 8/2007 | Gelbart et al. |
| 2007/0208330 A1 | 9/2007 | Treat et al. |
| 2007/0213710 A1 | 9/2007 | Lindenbaum et al. |
| 2007/0233185 A1 | 10/2007 | Anderson et al. |
| 2007/0282975 A1 | 12/2007 | Kato |
| 2008/0009747 A1 | 1/2008 | Saadat et al. |
| 2008/0015569 A1 | 1/2008 | Saadat et al. |
| 2008/0039793 A1 | 2/2008 | Goldman et al. |
| 2008/0039829 A1 | 2/2008 | Goldman et al. |
| 2008/0065150 A1 | 3/2008 | Drasler et al. |
| 2008/0082122 A1 | 4/2008 | Khosravi et al. |
| 2008/0091193 A1 | 4/2008 | Kauphusman et al. |
| 2008/0154303 A1 | 6/2008 | Yassinzadeh |
| 2008/0167643 A1 | 7/2008 | Mizrahi et al. |
| 2008/0177300 A1 | 7/2008 | Mas et al. |
| 2009/0125056 A1 | 5/2009 | Buchbinder et al. |
| 2009/0149847 A1 | 6/2009 | Yadin et al. |
| 2009/0163903 A1 | 6/2009 | Lindenbaum et al. |
| 2010/0228241 A1 | 9/2010 | Eckhouse et al. |

FOREIGN PATENT DOCUMENTS

| | | |
|---|---|---|
| DE | 3838840 A1 | 5/1990 |
| EP | 0075860 A2 | 4/1983 |
| EP | 0476178 A1 | 3/1992 |
| EP | 0482350 B1 | 4/1992 |
| EP | 0521595 B1 | 1/1993 |
| EP | 1096884 B1 | 5/2001 |
| EP | 1368089 A1 | 12/2003 |
| EP | 1599239 A2 | 11/2005 |
| EP | 1711117 B1 | 10/2006 |
| GB | 1 511 557 A | 5/1978 |
| GB | 2 054 385 A | 2/1981 |
| GB | 2 060 397 A | 5/1981 |
| JP | 3-080847 A | 4/1991 |
| JP | 5-337131 A | 12/1993 |
| JP | 6-233779 A | 8/1994 |
| JP | 8-501947 A | 3/1996 |
| JP | 2001-190561 A | 7/2001 |
| JP | 2002-301088 A | 10/2002 |
| JP | 2003-067676 A | 3/2003 |
| JP | 2003-220074 A | 8/2003 |
| KR | 100944676 B1 | 3/2010 |
| WO | WO-90/14796 A1 | 12/1990 |
| WO | WO-92/05740 A1 | 4/1992 |
| WO | WO-92/22252 A1 | 12/1992 |
| WO | WO-93/21844 A1 | 11/1993 |
| WO | WO-94/01158 A1 | 1/1994 |
| WO | WO-94/01199 A2 | 1/1994 |
| WO | WO-94/24948 A1 | 11/1994 |
| WO | WO-9632882 A1 | 10/1996 |
| WO | WO-97/09934 A1 | 3/1997 |
| WO | WO-98/11830 A1 | 3/1998 |
| WO | WO-9913779 A2 | 3/1999 |
| WO | WO-00/02488 A1 | 1/2000 |
| WO | WO-02/072188 | 9/2002 |
| WO | WO-2004/069300 A2 | 8/2004 |
| WO | WO-2004/069400 A1 | 8/2004 |
| WO | WO-2004/071612 A2 | 8/2004 |

| | | |
|---|---|---|
| WO | WO-2005/074364 A2 | 8/2005 |
| WO | WO-2006/054170 A1 | 5/2006 |
| WO | WO-2007/010391 A1 | 1/2007 |
| WO | WO-2009/023866 A1 | 2/2009 |
| WO | WO-2009/046356 A1 | 4/2009 |

OTHER PUBLICATIONS

U.S. Appl. No. 60/935,484, filed Aug. 15, 2007, Mizrahi et al.
U.S. Appl. No. 60/960,604, filed Oct. 5, 2007, Mizrahi et al.
U.S. Appl. No. 61/006,926, filed Feb. 6, 2008, Mizrahi et al.
U.S. Appl. No. 09/598,232, filed Jun. 21, 2000, Zucker.
"About AVD", http://www.compressar.com/about/index.shtml; Advanced Vascular Dynamics; last accessed Jun. 22, 2009; (Copyright (2006)); (p. 1).
"Overview of CompressorAR®," http://www.compressar.com/products/index.shtml; Advanced Vascular Dynamics; (Copyright (2002)); (p. 1).
Abbott Vascular Devices—ProStar XL 10 www.perclose.com/products/product.php?id=19; last accessed Dec. 5, 2005; (Copyright 1996, 2004); (p. 1).
Sigel et al., "The Mechanism of Blood Vessel Closure by High Frequency Electrocoagulation", Surgery Gynecology & Obstetrics; (Oct. 1965); vol. 121, No. 4; (pp. 823-831).
K.K. Jain, et al., "Repair of small blood vessels with the Neodymium-YAG laser: A preliminary report", *Surgery*, vol. 85, No. 6; (1979) (pp. 684-688).
S. Silber, et al., "Vascular Closure Devices for Immediate Sheath Removal after Coronary Interventions: Luxury or Necessity?",ISBN 0-683-30729-0, *Handbook of Coronary Stents*, 3. ed.; (2000); pp. 147-151.
International Search Report in co-pending application No. PCT/IL04/00100; Dated: Oct. 15, 2004.
Angio-Seal™, 111, 2002, STS Platform Design.
European Search Report in co-pending application No. 02703826.4; Dated: Feb. 6, 2009.
European Search Report in co-pending application No. 99929684.1; Dated: Apr. 6, 2004.
International Search Report in co-pending application No. PCT/IL05/00122; Dated: Dec. 30, 2005.
International Search Report in co-pending application No. PCT/IB05/03491; Dated: Feb. 27, 2006.
International Search Report in co-pending application No. PCT/IL02/00200; Dated: Jul. 31, 2002.
International Search Report in co-pending application No. PCT/IL97/00309; Dated: Feb. 3, 1998.
International Search Report in co-pending application No. PCT/IL99/00384; Dated: Nov. 9, 1999.
International Search Report in co-pending application No. PCT/US08/73402; Dated: Oct. 22, 2008.
International Search Report in co-pending application No. PCT/US08/78826; Dated: Dec. 29, 2008.
European Search Report in co-pending application No. EP 08798045.4 issued Jul. 27, 2011.
Japanese Office Action in co-pending application No. JP 2007-542157 issued Feb. 1, 2012.
Canadian Office Action in co-pending application No. CA 2,514,865 issued Feb. 7, 2012.
European Office Action in co-pending application No. EP 05 703 165.0 issued Mar. 29, 2010.
European Office Action in co-pending application No. EP 05 703 165.0 issued Dec. 21, 2009.
European Office Action in co-pending application No. EP 04 707 612.0 issued Sep. 7, 2011.
Korean Notice of Grounds for Refusal in co-pending application No. 10-2003-7012034 issued Dec. 14, 2007.
Korean Notice of Grounds for Refusal in co-pending application No. 10-2003-7012034 issued Jun. 16, 2008.
Korean Notice of Grounds for Refusal in co-pending application No. 10-2003-7012034 issued Feb. 24, 2009.
In the U.S. Patent and Trademark Office, Non-Final Office Action in re: U.S. Appl. No. 11/791,448, dated Feb. 7, 2012, 12 pages.
In the U.S. Patent and Trademark Office, Non-Final Office Action in re: U.S. Appl. No. 10/543,654, dated Aug. 26, 2009, 11 pages.
In the U.S. Patent and Trademark Office, Final Office Action in re: U.S. Appl. No. 10/543,654, dated Jul. 7, 2010, 10 pages.
In the U.S. Patent and Trademark Office, Examiner's Interview Summary in re: U.S. Appl. No. 10/543,654, dated Aug. 10, 2010, 3 pages.
In the U.S. Patent and Trademark Office, Restriction Requirement in re: U.S. Appl. No. 10/543,654, dated Jan. 22, 2009, 6 pages.
In the U.S. Patent and Trademark Office, Non-Final Office Action in re: U.S. Appl. No. 10/543,654, dated Oct. 26, 2009, 12 pages.
In the U.S. Patent and Trademark Office, Final Office Action in re: U.S. Appl. No. 10/543,654, dated Jul. 7, 2010, 11 pages.
In the U.S. Patent and Trademark Office, Examiner Interview Summary in re: U.S. Appl. No. 09/114,817, dated Oct. 20, 1999, 1 page.
In the U.S. Patent and Trademark Office, Non-Final Office Action in re: U.S. Appl. No. 09/114,817, dated Aug. 24, 1999, 5 pages.
In the U.S. Patent and Trademark Office, Examiner;s Interview Summary in re: U.S. Appl. No. 10/288,843, dated Mar. 1, 2005, 1 page.
In the U.S. Patent and Trademark Office, Non-Final Office Action in re: U.S. Appl. No. 10/288,843, dated Jan. 11, 2005, 4 pages.
In the U.S. Patent and Trademark Office, Notice of Allowance in re: U.S. Appl. No. 09/808,630, dated Oct. 6, 2003, 9 pages.
In the U.S. Patent and Trademark Office, Non-Final Office Action in re: U.S. Appl. No. 09/808,630, dated Sep. 17, 2003, 1 page.
In the U.S. Patent and Trademark Office, Non-Final Office Action in re: U.S. Appl. No. 09/808,630, dated Nov. 25, 2002, 5 pages.
In the U.S. Patent and Trademark Office, Final Office Action in re: U.S. Appl. No. 11/797,294, dated Jul. 26, 2011, 17 pages.
In the U.S. Patent and Trademark Office, Examiner's Interview Summary in re: U.S. Appl. No. 11/797,294, dated Jun. 17, 2010, 4 pages.
In the U.S. Patent and Trademark Office, Notice of Allowance in re: U.S. Appl. No. 09/114,817, dated Dec. 16, 1999, 5 pages.
In the U.S. Patent and Trademark Office, Restriction Requirement in re: U.S. Appl. No. 09/598,232, dated Jun. 5, 2002, 4 pages.
In the U.S. Patent and Trademark Office, Non-Final Office Action in re: U.S. Appl. No. 09/598,232, dated Jul. 16, 2002, 7 pages.
In the U.S. Patent and Trademark Office, Notice of Allowance in re: U.S. Appl. No. 10/288,843, dated Jul. 6, 2005, 6 pages.
In the U.S. Patent and Trademark Office, Non-Final Office Action in re: U.S. Appl. No. 09/808,630, dated Aug. 18, 2003, 5 pages.
In the U.S. Patent and Trademark Office, Restriction Requirement in re: U.S. Appl. No. 09/808,630, dated Jun. 26, 2002, 4 pages.
In the U.S. Patent and Trademark Office, Non-Final Office Action in re: U.S. Appl. No. 11/791,277 dated Apr. 20, 2011, 9 pages.
In the U.S. Patent and Trademark Office, Final Office Action in re: U.S. Appl. No. 11/791,277 dated Dec. 6, 2011, 12 pages.
In the U.S. Patent and Trademark Office, Final Office Action in re: U.S. Appl. No. 08/715,160, dated Jul. 9, 1997, 7 pages.
In the U.S. Patent and Trademark Office, Non-Final Office Action in re: U.S. Appl. No. 08/715,160, dated Feb. 26, 1997, 6 pages.
In the U.S. Patent and Trademark Office, Notice of Allowance in re: U.S. Appl. No. 08/715,160, dated Oct. 2, 1997, 7 pages.
In the U.S. Patent and Trademark Office, Examiner's Interview Summary in re: U.S. Appl. No. 08/715,160, dated Sep. 29, 1997, 6 pages.
In the U.S. Patent and Trademark Office,Non- Final Office Action in re: U.S. Appl. No. 11/471,537, dated Sep. 4, 2008, 6 pages.
In the U.S. Patent and Trademark Office, Non-Final Office Action in re: U.S. Appl. No. 11/797,294, dated Nov. 13, 2008, 12 pages.
In the U.S. Patent and Trademark Office, Final Office Action in re: U.S. Appl. No. 11/797,294, dated Jul. 7, 2009, 12 pages.
In the U.S. Patent and Trademark Office, Non-Final Office Action in re: U.S. Appl. No. 11/797,294, dated Jan. 15, 2010, 12 pages.
In the U.S. Patent and Trademark Office, Final Office Action in re: U.S. Appl. No. 11/797,294, dated Aug. 24, 2010, 12 pages.
In the U.S. Patent and Trademark Office, Non-Final Office Action in re: U.S. Appl. No. 11/797,294, dated Feb. 25, 2011, 16 pages.
In the U.S. Patent and Trademark Office, Examiner's Interview Summary in re: U.S. Appl. No. 10/358,130, dated Dec. 7, 2005, 1 page.
In the U.S. Patent and Trademark Office, Non-Final Office Action in re: U.S. Appl. No. 10/616,887, dated Aug. 24, 2005, 7 pages.
In the U.S. Patent and Trademark Office, Final Office Action in re: U.S. Appl. No. 10/616,887, dated May 22, 2006, 7 pages.
In the U.S. Patent and Trademark Office, Notice of Allowance in re: U.S. Appl. No. 10/616,887, dated Jan. 24, 2007, 8 pages.

In the U.S. Patent and Trademark Office, Examiner's Interview Summary in re: U.S. Appl. No. 10/616,887, dated Jun. 26, 2006, 3 pages.
In the U.S. Patent and Trademark Office, Examiner's Interview Summary in re: U.S. Appl. No. 10/616,887, dated Mar. 1, 2006, 3 pages.
In the U.S. Patent and Trademark Office, Restriction Requirement in re: U.S. Appl. No. 10/616,887, dated May 31, 2005, 5 pages.
In the U.S. Patent and Trademark Office, Restriction Requirement in re: U.S. Appl. No. 12/192,911, dated Sep. 13, 2011, 11 pages.
In the U.S. Patent and Trademark Office, Restriction Requirement in re: U.S. Appl. No. 12/245,569, dated Apr. 14, 2011, 9 pages.
In the U.S. Patent and Trademark Office, Non-Final Office Action in re: U.S. Appl. No. 12/245,569, dated Jul. 14, 2011, 9 pages.
In the U.S. Patent and Trademark Office, Final Office Action in re: U.S. Appl. No. 12/245,569, dated Nov. 30, 2011, 8 pages.
In the U.S. Patent and Trademark Office, Non-Final Office Action in re: U.S. Appl. No. 12/192,911, dated Apr. 26, 2012, 28 pages.
European Search Report in co-pending application No. EP 08836162 issued May 10, 2012.

* cited by examiner

METHODS AND APPARATUS FOR HEMOSTASIS FOLLOWING ARTERIAL CATHETERIZATION

CROSS REFERENCE TO RELATED APPLICATIONS

This application is a continuation of U.S. application Ser. No. 11/797,294, filed May 2, 2007, now abandoned, which is a continuation U.S. application Ser. No. 10/616,887, filed Jul. 10, 2003, now U.S. Pat. No. 7,223,266, which is a continuation-in-part of U.S. application Ser. No. 10/358,130, filed Feb. 4, 2003, now U.S. Pat. No. 7,115,127, the contents of each are incorporated by reference.

FIELD OF THE INVENTION

The present invention relates to catheterization systems and methodologies generally and more particularly to post-catheterization closure.

BACKGROUND OF THE INVENTION

Various techniques are known for arterial catheterization. Following arterial catheterization, it is necessary to promote hemostasis quickly and without undue hardship for the patient.

Applicant's U.S. Pat. Nos. 5,728,134 and 6,048,358, and Published PCT Patent Applications WO 98/11830 and WO 00/02488 describe methods and apparatus for hemostasis that greatly simplifies hemostasis and thus greatly reduces patient discomfort following arterial catheterization. These patent documents, the disclosure of which are hereby incorporated by reference, and the prior art referenced therein are considered to represent the state of the art.

SUMMARY OF THE INVENTION

The present invention seeks to provide improved systems and methodologies for post-catheterization closure.

There is thus provided in accordance with a preferred embodiment of the present invention a method for producing hemostasis of an artery of a patient having a puncture following arterial catheterization including introducing a hemostasis device including at least one electrode into the vicinity of the puncture, supplying an electric current to the at least one electrode, thereby heating a volume of blood in the vicinity of the puncture, causing coagulation of the blood and causing closure of the puncture and subsequently removing the hemostasis device from the patient.

In accordance with another preferred embodiment of the present invention the at least one electrode includes a pair of electrodes.

In accordance with yet another preferred embodiment of the present invention the introducing includes introducing via a catheter introducer. Additionally, the introducing also includes inflating an anchor balloon attached to an end of the hemostasis device. Alternatively or additionally, the introducing also includes inflating a peripheral balloon. In accordance with still another preferred embodiment of the present invention the removing the hemostasis device includes deflating the peripheral balloon.

In accordance with another preferred embodiment of the present invention the introducing also includes positioning the at least one electrode in close proximity to the volume of blood.

Preferably, the supplying includes supplying electrical power at RF frequencies. Additionally, the electrical power includes electrical power in the range of 0.1-10 watts at up to 25 volts.

In accordance with yet another preferred embodiment of the present invention the supplying also includes adjusting the electric current based on a feedback measurement.

There is also provided in accordance with another preferred embodiment of the present invention a hemostasis device including a main shaft, at least one balloon and at least one electrode, operable to supply an electric current and to thereby heat a volume of blood adjacent to the at least one electrode and to cause coagulation of the blood and closure of the puncture.

In accordance with another preferred embodiment of the present invention the at least one balloon includes at least one anchor balloon, disposed at an end of the main shaft and at least one peripheral balloon, disposed at a location along the main shaft exterior to a wall of the main shaft. Preferably, the volume of blood is delimited by the peripheral balloon and a wall of the artery.

In accordance with yet another preferred embodiment of the present invention the hemostasis device also includes an electrical power source and control module. Additionally, the electrical power source and control module includes a power supply, operative to supply power to the at least one electrode, feedback measurement means and a processor.

Preferably, the power supply includes an RF power supply which supplies electrical power at RF frequencies within a range of 0.1-10 watts at up to 25 volts.

In accordance with still another preferred embodiment of the present invention the feedback measurement means is operative to measure at least one of electrical current, blood resistance and blood temperature.

Additionally, the processor is operative to adjust the power based on an output from the feedback measurement means.

In accordance with yet another preferred embodiment of the present invention the at least one electrode includes a pair of electrodes.

There is further provided in accordance with yet another preferred embodiment of the present invention a method for producing hemostasis of an artery of a patient having a puncture following arterial catheterization, including introducing a hemostasis device including at least one electrode into the vicinity of the puncture, positioning the at least one electrode in proximity with the puncture, supplying an electric current to the at least one electrode, thereby heating a volume of blood in the vicinity of the puncture, causing coagulation of the blood and causing closure of the puncture and subsequently removing the hemostasis device from the patient.

In accordance with another preferred embodiment of the present invention the positioning includes inflating an anchor balloon attached to an end of the hemostasis device, inflating a peripheral balloon and subsequently deflating the anchor balloon. Preferably, the volume of blood is delimited by the peripheral balloon and a wall of the artery.

In accordance with still another preferred embodiment of the present invention the at least one electrode includes a pair of electrodes.

In accordance with yet another preferred embodiment of the present invention the supplying includes supplying electrical power at RF frequencies. Additionally, the electrical power includes electrical power in the range of 0.1-10 watts at up to 25 volts.

In accordance with another preferred embodiment of the present invention the supplying also includes adjusting the electric power based on a feedback measurement.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
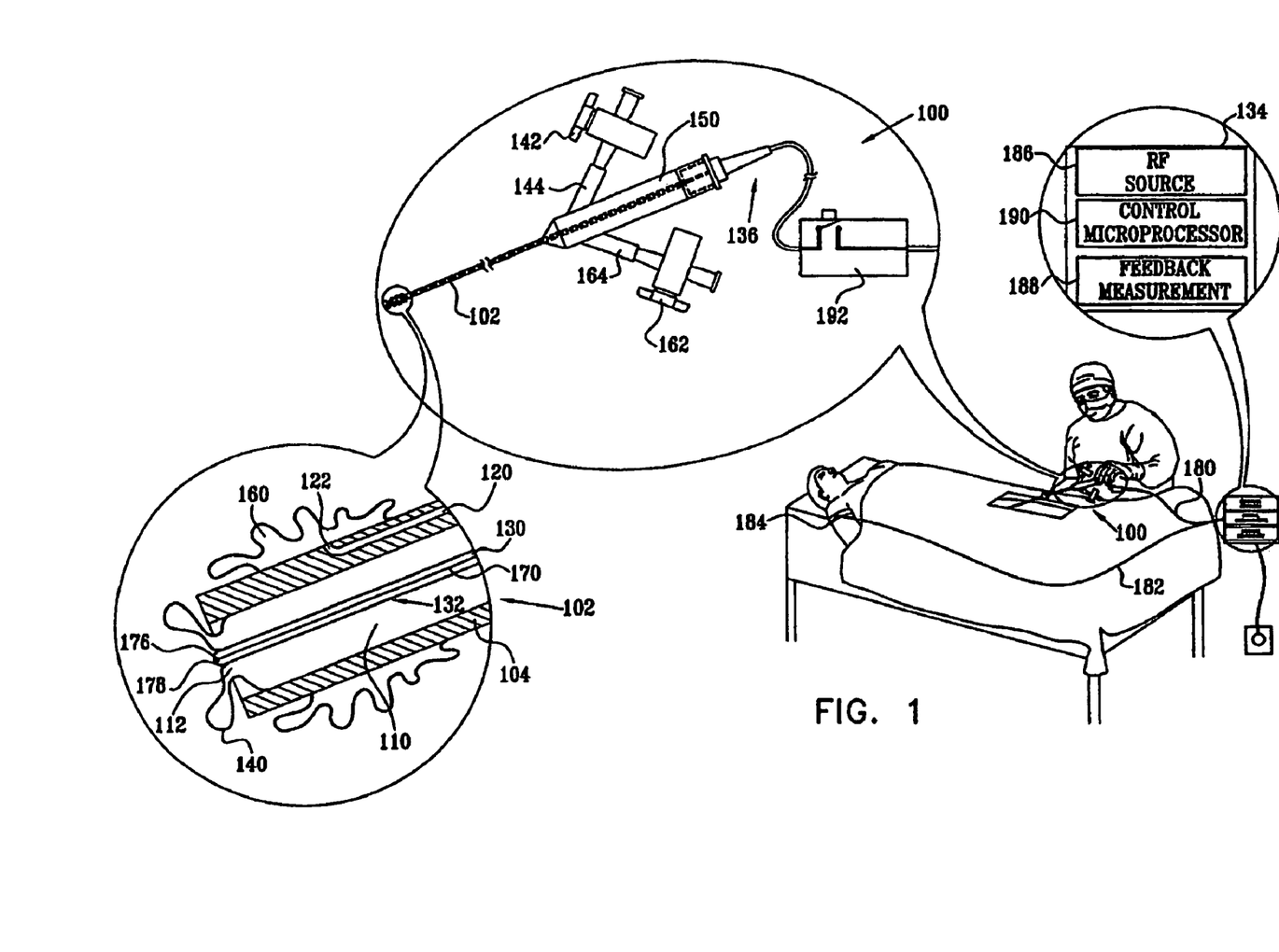
FIG. 1 is a simplified illustration of a hemostasis device constructed and operative in accordance with a preferred embodiment of the present invention.

Reference is now made to FIG. 1, which is a simplified illustration of a hemostasis device 100 for producing hemostasis following arterial catheterization, in accordance with a preferred embodiment of the present invention. The hemostasis device 100 is suitable for insertion via a conventional catheter introducer (not shown) following completion of catheterization and removal of the catheter from the catheter introducer.

In accordance with a preferred embodiment of the present invention, hemostasis device 100 comprises a main shaft 102, which has an outer wall 104 and preferably includes at least three bores. A first bore, designated generally by reference numeral 110, extends along the main shaft 102 to an anchor balloon inflation location 112. A second bore 120 extends along the shaft 102 to a peripheral balloon inflation location 122. A third bore, designated generally by reference number 130, contains an electrocoagulation heating device 132 connected to an electrical power source and control module 134 by a connector 136.

Disposed at an end of main shaft 102 at anchor balloon inflation location 112 is an anchor balloon 140. Anchor balloon 140 is selectably inflated, as shown in FIG. 2C, via a stopcock 142 and associated conduit 144 in fluid communication with main shaft 102 via a head element 150. Head element 150 is fixed to main shaft 102 at an end thereof opposite the end at which anchor balloon 140 is located. The interior of head element 150 is in fluid communication with first bore 110 in main shaft 102, which in turn is in fluid communication with the interior of the anchor balloon 140 at anchor balloon inflation location 112.

Disposed adjacent the end of second bore 120 in fluid communication with peripheral balloon inflation location 122, exterior of wall 104, is a peripheral balloon 160. Peripheral balloon 160 is selectably inflated, as shown in FIG. 2E, via second bore 120, via a stopcock 162 and associated conduit 164 that communicate with second bore 120 via head element 150.

In accordance with a preferred embodiment of the present invention, electrocoagulation heating device 132 comprises an electrical conductor 170 connected to an electrocoagulation electrode 176 at an extreme end 178 of third bore 130. A pair of electrical cables 180 and 182 extend from electrical power source and control module 134. In the illustrated embodiment, electrical cable 180 serves as a power supply cable and is connected to electrocoagulation heating device 132 by connector 136. Electrical cable 182 serves as a return current cable and is preferably connected to an electrode 184 attached to a body of a patient.

Electrical power source and control module 134 preferably comprises a power supply, preferably an RF power supply source 186, including a feedback measurement circuit 188. The feedback measurement circuit 188 is preferably operative to measure current, blood resistance or blood temperature and thereby determine progress of hemostasis. The electrical power source and control module 134 also preferably includes a microprocessor 190, operative to adjust the power supplied to hemostasis device 100 according to the blood temperature or other feedback measurement received from feedback measurement circuit 188, in order to achieve optimal coagulation of the blood.

In accordance with a preferred embodiment of the present invention an operator actuation switch 192 is connected along electrical cable 180. In accordance with another preferred embodiment, switch 192 may be obviated and electrical cable 180 connected directly to connector 136.

Reference is now made to FIGS. 2A-2I, which illustrate various steps in a preferred mode of operation of the apparatus of FIG. 1.

Figure 2A:
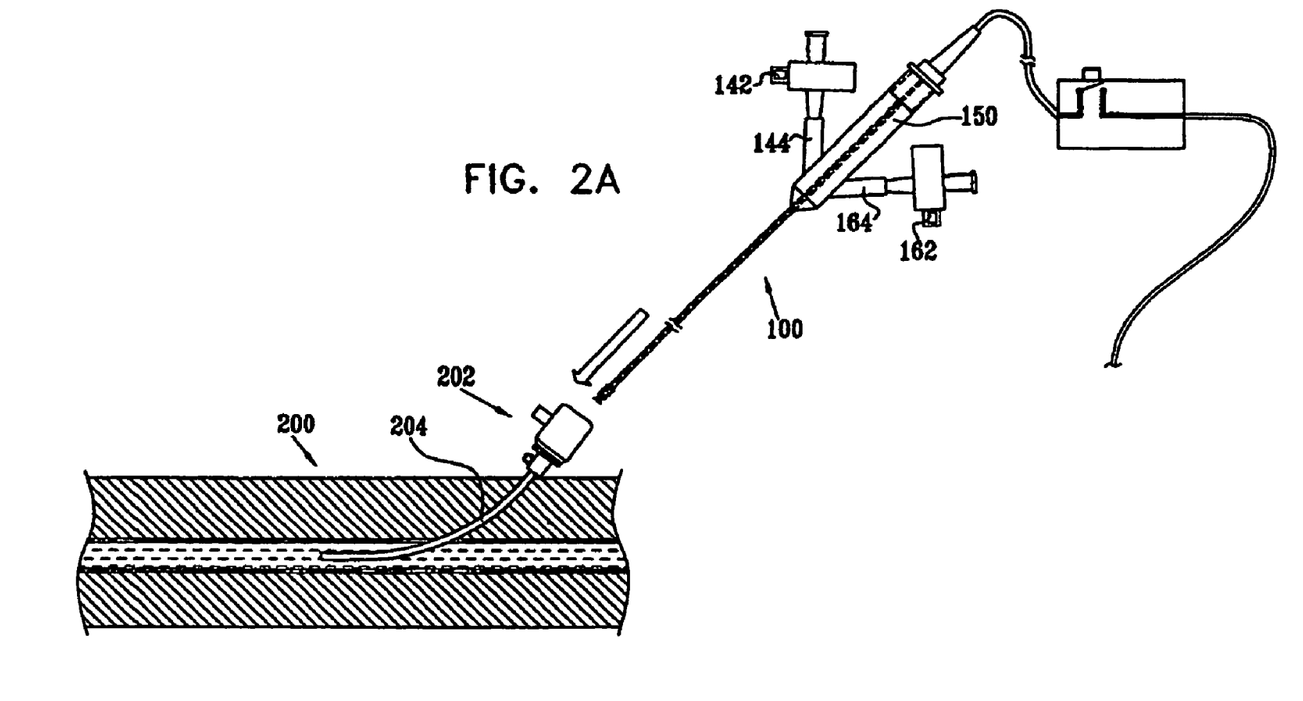
FIGS. 2A, 2B, 2C, 2D, 2E, 2F, 2G, 2H and 2I are simplified illustrations of the operation of the apparatus of FIG. 1 in a patient treatment context.
Figure 2B:
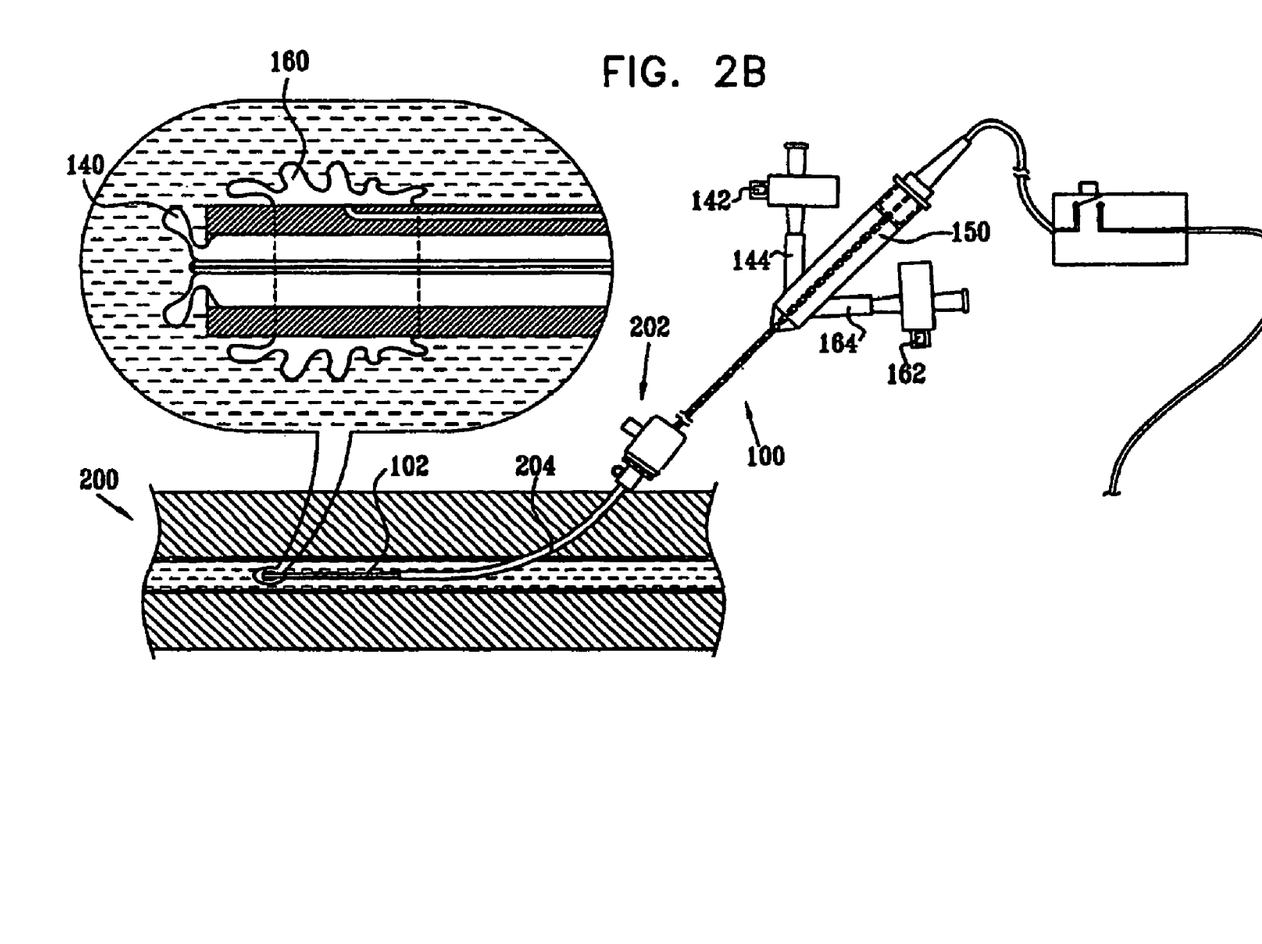
Figure 2C:
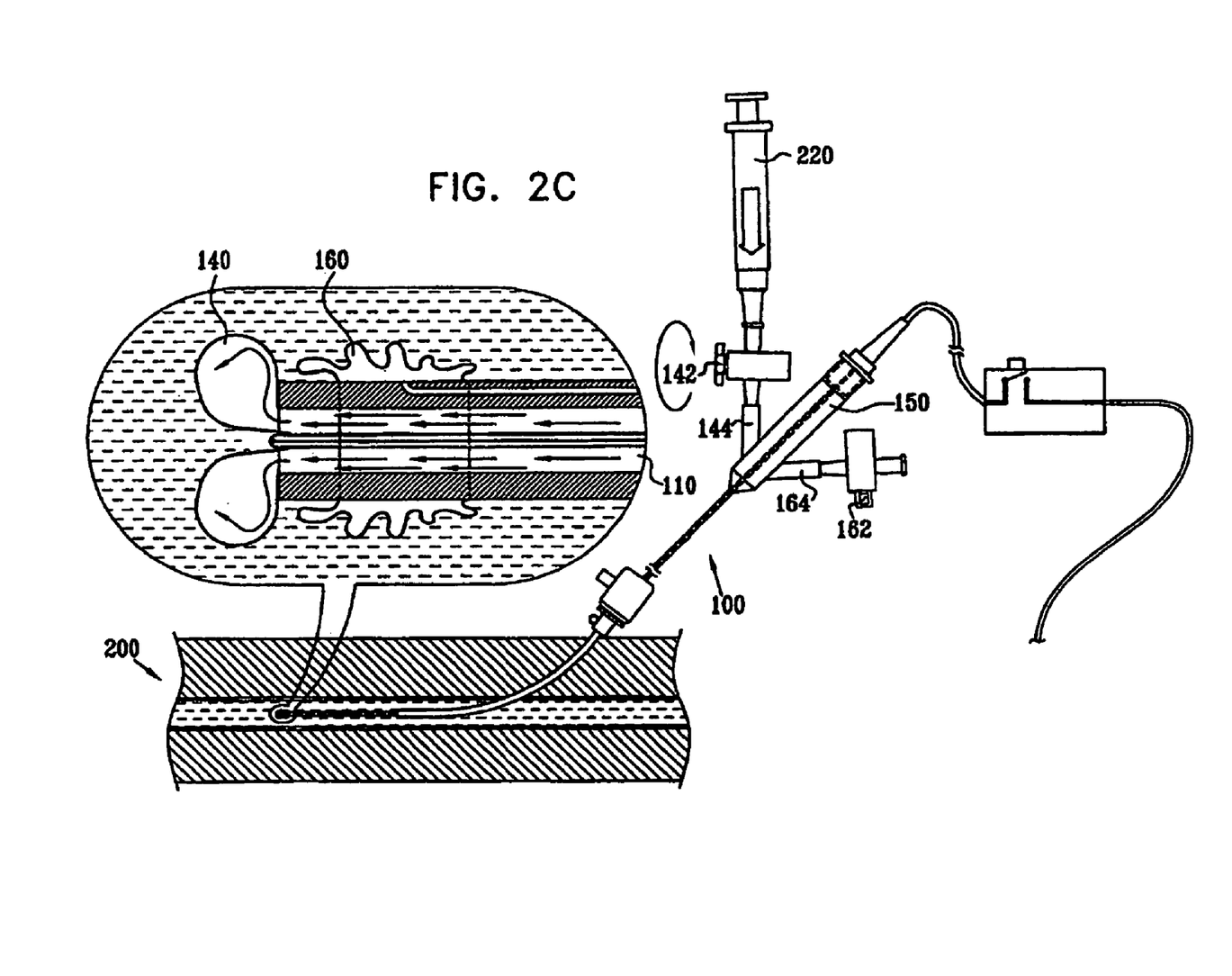

FIG. 2A illustrates the hemostasis device 100 about to be inserted into an artery 200 via a conventional catheter introducer assembly 202, following completion of a catheterization procedure and withdrawal of a catheter (not shown) from the catheter introducer assembly 202. The catheter introducer assembly 202 conventionally includes a catheter introducer sheath 204.

FIG. 23 shows the hemostasis device 100 inserted into the catheter introducer assembly 202 such that the outer end of the main shaft 102 extends into the artery 200 well beyond the end of catheter introducer sheath 204. As shown with particularity in FIG. 2B, at this stage both anchor balloon 140 and peripheral balloon 160 are deflated.

Reference is now made to FIG. 2C, which shows initial inflation of the anchor balloon 140, preferably by use of a syringe 220 communicating with first bore 110 via the interior of head element 150, stopcock 142 and associated conduit 144. The inflated anchor balloon 140 preferably has a cusp-type configuration as seen with particularity in FIG. 2C.

Figure 2D:
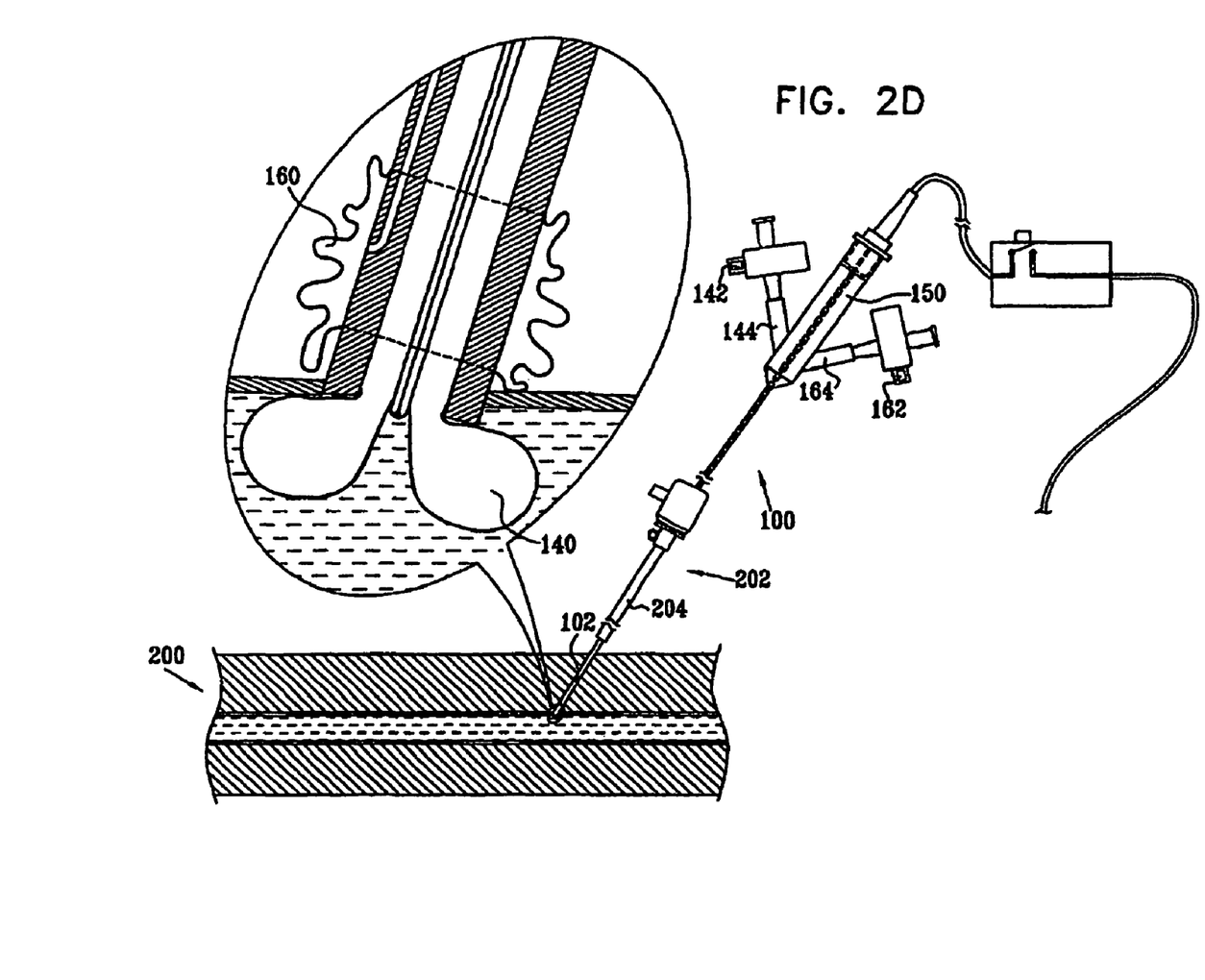
Figure 2E:
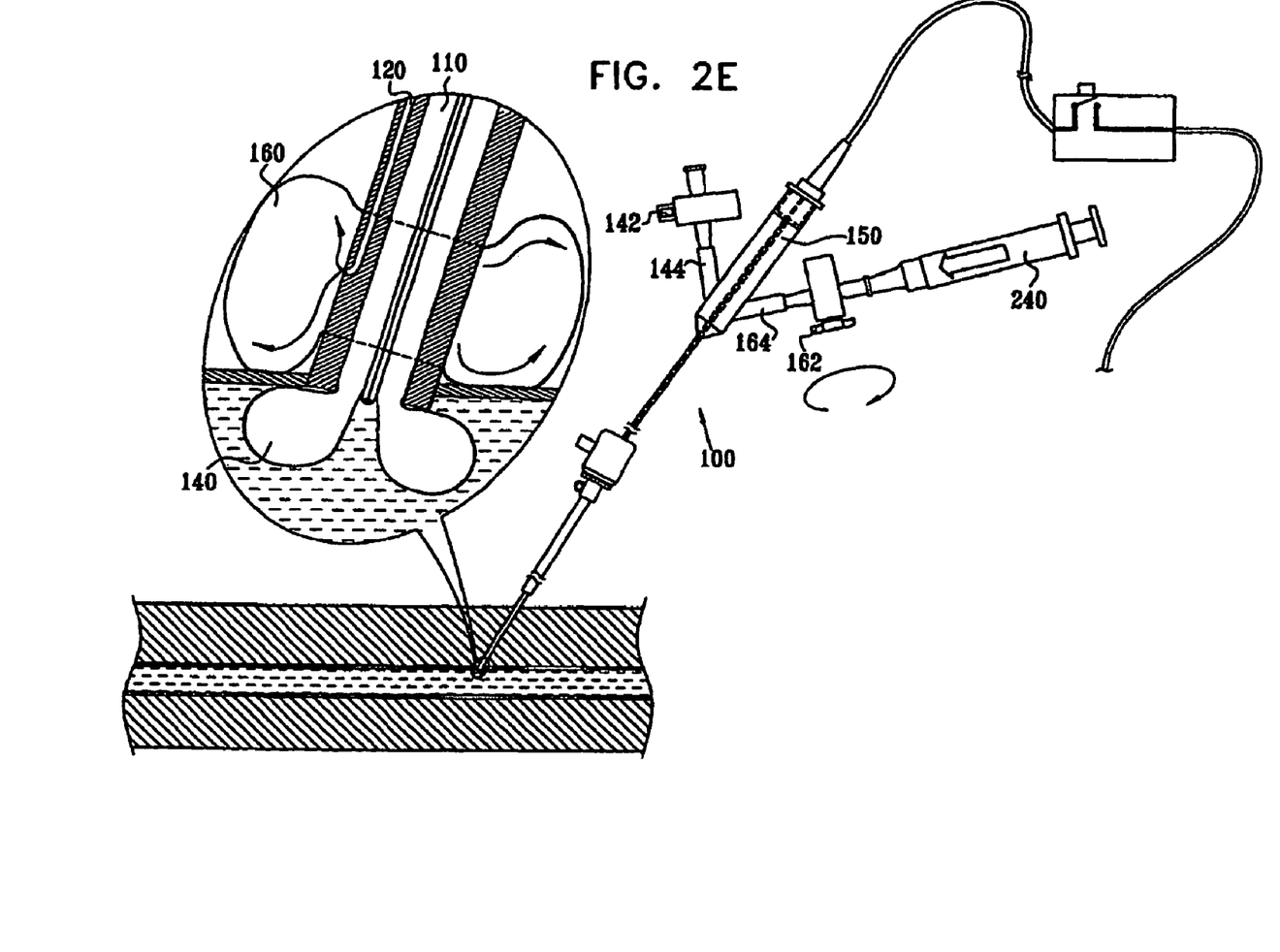

Following inflation of the anchor balloon 140, the catheter introducer assembly 202 and the hemostasis device 100 are both withdrawn, such that the catheter introducer sheath 204 is removed from artery 200 only when the anchor balloon 140 already engages the interior wall of artery 200 in sealing engagement with the aperture in the artery 200 through which the catheter introducer sheath 204 is drawn and through which the main shaft 102 presently extends. This stage is shown in FIG. 2D.

As seen in FIG. 2E, initial inflation of the peripheral balloon 160 is effected, preferably by use of a syringe 240 communicating with second bore 120 via head element 150, stopcock 162 and associated conduit 164.

Figure 2F:
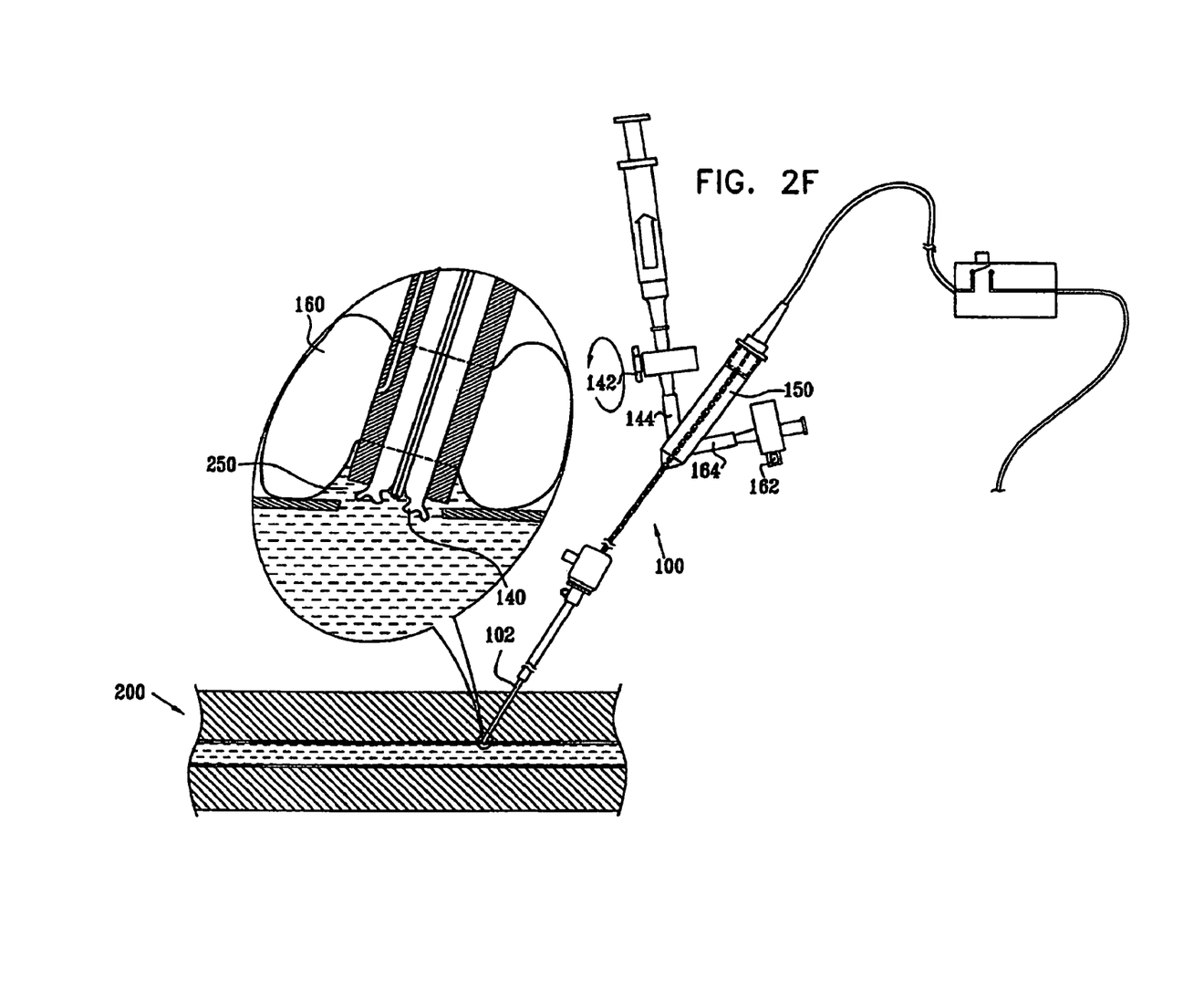

Thereafter, as seen in FIG. 2F, the anchor balloon 140 is deflated and the peripheral balloon 160 is more fully inflated, which preferably causes the extreme end of the main shaft 102 to be withdrawn from the artery 200 to a location lying just outside the artery wall. As seen in FIG. 2F, peripheral balloon 160 is preferably designed to allow a limited volume of blood to collect outside of the artery wall after the anchor balloon 140 is deflated. This volume of blood is located in a region, indicated by reference numeral 250, delimited by the engagement of peripheral balloon 160 with the artery wall.

Figure 2G:
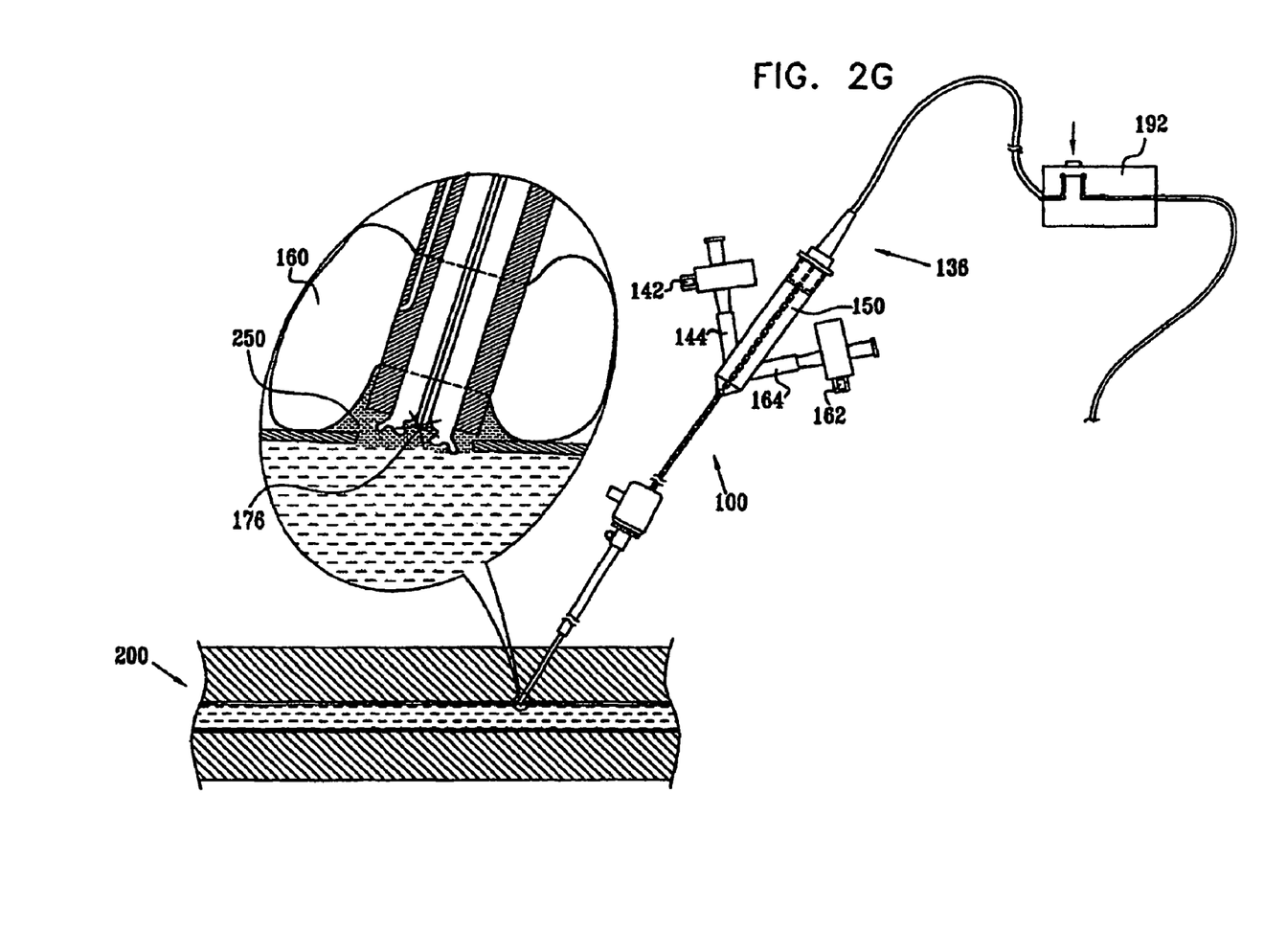

At this stage, electric power is supplied to the electrode 176 to provide heating of the blood in region 250, causing coagulation thereof, as seen in FIG. 2G. In accordance with the illustrated embodiment of FIG. 1 and as shown in FIG. 2G, the electric power is provided by actuation of switch 192. In accordance with another preferred embodiment, switch 192 is obviated, and the electric power is provided by connecting electrical cable 180 (FIG. 1) directly to connector 136.

Preferably, the amount of electrical power supplied along electrical cable 180 (FIG. 1) from electrical power source and control module 134 to the electrocoagulation electrode 176 is between 0.1-10 watts at up to 25 volts at RF frequencies.

Figure 2H:
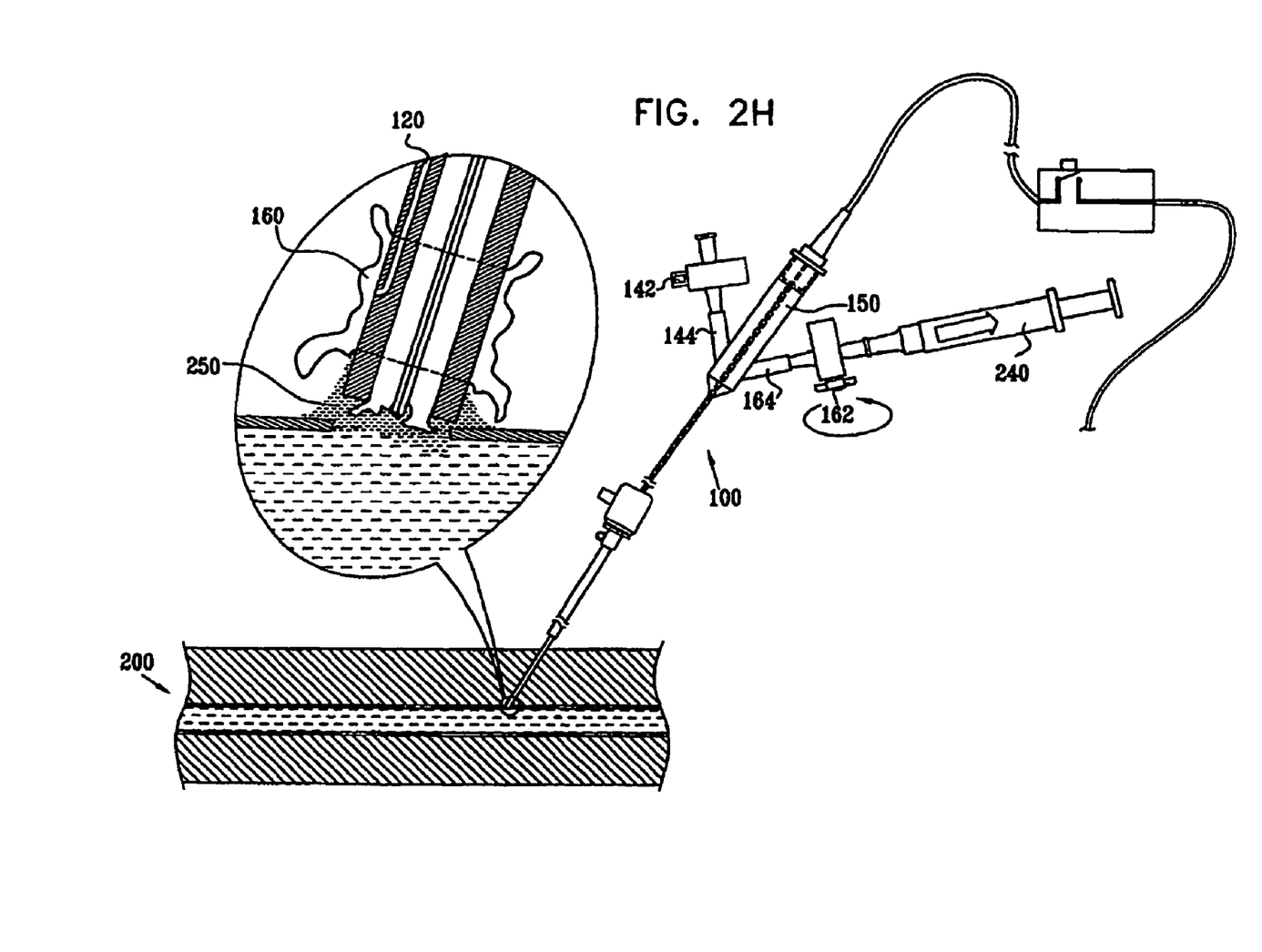

Once acceptable hemostasis has occurred in region 250, the peripheral balloon 160 is deflated, as shown in FIG. 2H, preferably by operation of syringe 240 communicating with second bore 120 via head element 150, stopcock 162 and associated conduit 164.

Figure 2I:
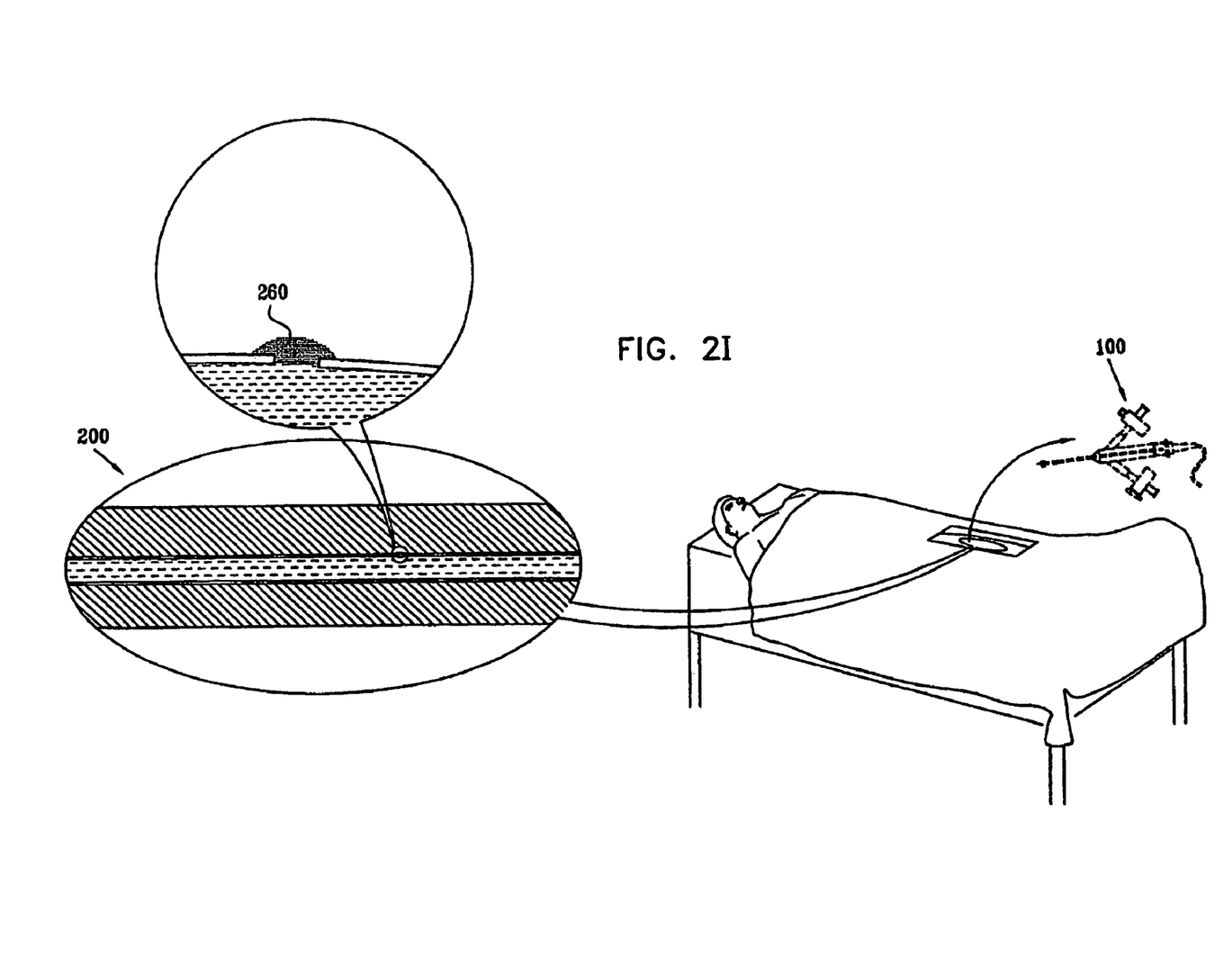

Thereafter, the hemostasis device 100 is entirely withdrawn from the patient, leaving a region 260 of hemostasis outside of artery 200, as shown in FIG. 2I.

Figure 3:
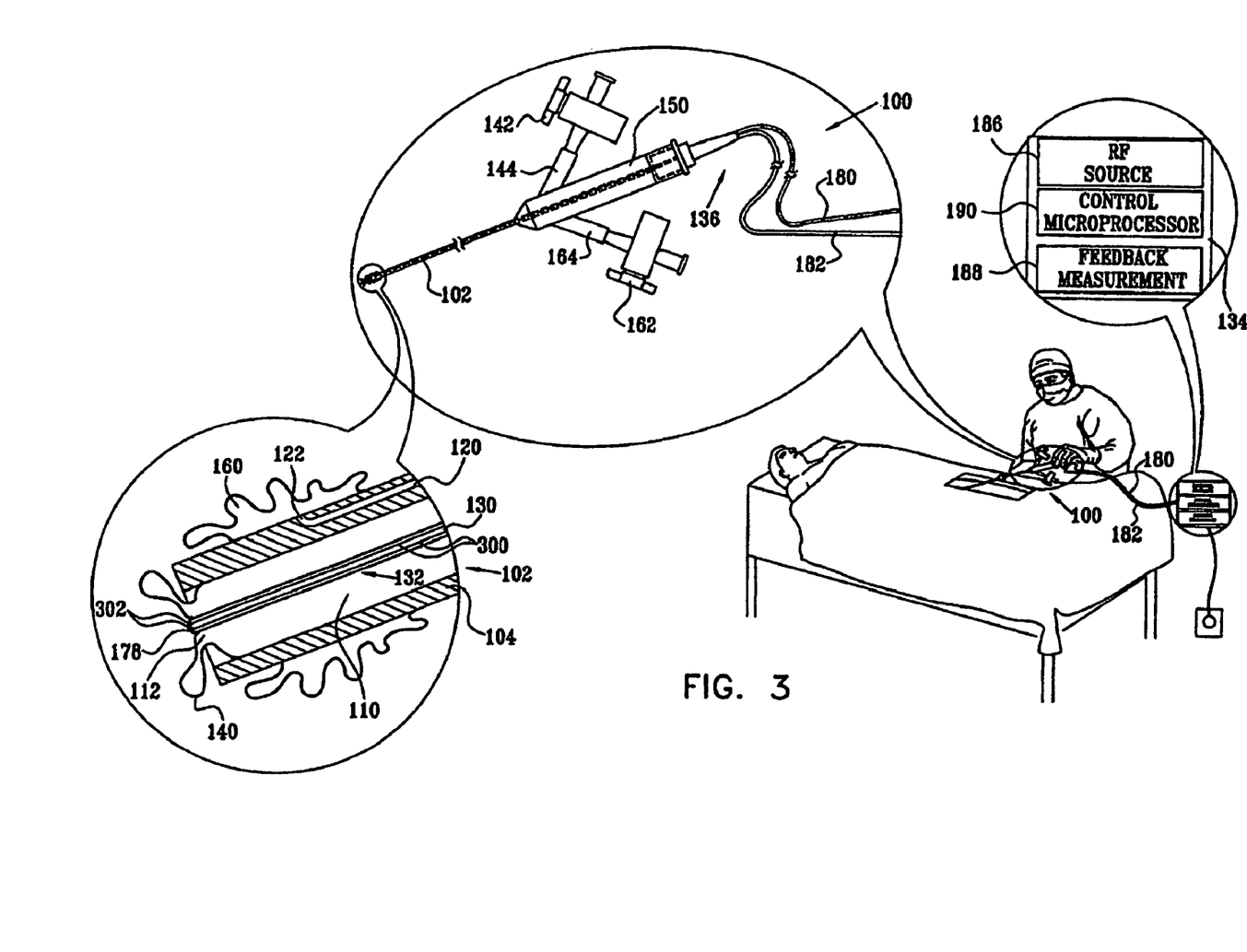
FIG. 3 is a simplified illustration of a hemostasis device constructed and operative in accordance with another preferred embodiment of the present invention.

Reference is now made to FIG. 3, which is a simplified illustration of a hemostasis device constructed and operative in accordance with another preferred embodiment of the present invention. The embodiment of FIG. 3 is similar to that of FIG. 1, except as described hereinbelow. Elements that occur in both embodiments are identified by the same reference numerals.

In the embodiment of FIG. 3, electrocoagulation heating device 132 comprises a pair of separate electrical conductors 300 extending along third bore 130 connecting electrical power source and control module 134 to a pair of electrocoagulation electrodes 302 at end 178 of third bore 130. Electrical cables 180 and 182 are both connected to electrocoagulation heating device 132 by connector 136. The illustrated embodiment shows connector 136 directly connected to electrical cables 180 and 182.

In the embodiment of FIG. 3, the electrodes 302 may be arranged in mutual coaxial arrangement or in mutual side-by-side arrangement or any other suitable arrangement.

It will be appreciated by persons skilled in the art that the present invention is not limited by what has been particularly shown and described hereinabove. Rather the scope of the present invention includes both combinations and subcombinations of the various features described hereinabove and shown in the drawings as well as modifications and further developments thereof which would occur to a person of ordinary skill in the art upon reading the foregoing description and which are not in the prior art.

The invention claimed is:

1. A method for producing hemostasis of an artery of a patient having a puncture following arterial catheterization comprising:
   introducing a hemostasis device into a vicinity of the puncture, the hemostasis device comprising:
      a main shaft;
      an expandable member disposed on the main shaft; and
      at least one electrode coupled to the main shaft;
   expanding the expandable member to form a region delimited by engagement of the expandable member against an outside of an artery wall;
   allowing a limited volume of blood to collect outside the artery wall and within the region;
   supplying an electric current to said at least one electrode, thereby heating the region causing coagulation of the limited volume of blood in the region and causing closure of said puncture; and
   subsequently removing said hemostasis device from the patient.

2. A method according to claim 1 and wherein said at least one electrode comprises a pair of electrodes.

3. A method according to claim 1 and wherein said introducing comprises introducing via a catheter introducer.

4. A method according to claim 1 and wherein said introducing also comprises inflating an anchor balloon attached to an end of said hemostasis device.

5. A method according to claim 4, further comprising deflating the anchor balloon.

6. A method according to claim 1 and wherein said removing of said hemostasis device comprises deflating said expandable member.

7. A method according to claim 1 and wherein said introducing also comprises positioning said at least one electrode in close proximity to the region.

8. A method according to claim 1 and wherein said supplying comprises supplying electrical power at RF frequencies.

9. A method according to claim 8 and wherein said electrical power comprises electrical power in the range of 0.1-10 watts at up to 25 volts.

10. A method according to claim 1 and wherein said supplying also comprises adjusting said electric current based on feedback measurement.

11. A method for producing hemostasis of an artery of a patient having a puncture following arterial catheterization comprising:
    introducing a hemostasis device into a vicinity of the puncture, the hemostasis device comprising:
       a main shaft;
       an expandable member disposed on the main shaft; and
       at least one electrode coupled to the main shaft;
    positioning said at least one electrode in proximity with said puncture;
    expanding the expandable member to form a region delimited by engagement of the expandable member against an outside of an artery wall;
    allowing a limited volume of blood to collect outside the artery wall and within the region;
    supplying an electric current to said at least one electrode, thereby heating the region, causing coagulation of the limited volume of blood in the region and causing closure of said puncture; and
    subsequently removing said hemostasis device from the patient.

12. A method according to claim 11 and wherein said positioning comprises:
    inflating an anchor balloon attached to an end of said hemostasis device;
    and subsequently deflating said anchor balloon.

13. A method according to claim 11 and wherein said at least one electrode comprises a pair of electrodes.

14. A method according to claim 11 and wherein said supplying comprises supplying electrical power at RF frequencies.

15. A method according to claim 14 and wherein said electrical power comprises electrical power in the range of 0.1-10 watts at up to 25 volts.

16. A method according to claim 11 and wherein said supplying also comprises adjusting said electric current based on a feedback measurement.

* * * * *